(12) United States Patent
Nozaki et al.

(10) Patent No.: US 7,288,412 B2
(45) Date of Patent: Oct. 30, 2007

(54) METHOD AND DEVICE FOR DETERMINING DISTRIBUTION OF GLYCATION OF ERYTHROCYTIC MEMBRANES

(76) Inventors: Osamu Nozaki, 29-4, Ohnodai 1-chome, Osakasayama-shi, Osaka (JP); Hiroko Kawamoto, 209-3, Nishikimachi 1-chome, Yonago-shi, Tottori (JP); Motonori Munesue, 178-11, Kitashinmachi 6-chome, Matsubara-shi, Osaka (JP)

( * ) Notice: Subject to any disclaimer, the term of this patent is extended or adjusted under 35 U.S.C. 154(b) by 389 days.

(21) Appl. No.: 10/903,077

(22) Filed: Jul. 30, 2004

(65) Prior Publication Data

US 2005/0026241 A1 Feb. 3, 2005

(30) Foreign Application Priority Data

Jul. 31, 2003 (JP) ............................. 2003-204441

(51) Int. Cl.
*G01N 33/48* (2006.01)
(52) U.S. Cl. ......................................... 436/63; 435/325
(58) Field of Classification Search ................ 435/325; 436/63
See application file for complete search history.

(56) References Cited

U.S. PATENT DOCUMENTS 4,452,773 A * 6/1984 Molday ...................... 424/1.37
5,968,820 A * 10/1999 Zborowski et al. ......... 435/325
6,162,645 A * 12/2000 Lee et al. ..................... 436/67

FOREIGN PATENT DOCUMENTS

JP 08-122335 A 5/1996
JP 09-178719 A 7/1997

OTHER PUBLICATIONS

Umudum, FZ et al. Erythrocyte membrane glycation and Na+-K+ levels in NIDDM. Journal of Diabetes and Its Complications. 2002. 16: 359-362.*

* cited by examiner

*Primary Examiner*—Leon B. Lankford, Jr.
*Assistant Examiner*—Susan E. Fernandez
(74) *Attorney, Agent, or Firm*—Akin Gump Strauss Hauer & Feld LLP

(57) ABSTRACT

A method for determining the distribution of glycation of erythrocytic membranes includes steps of bonding magnetic beads having a boric acid group with sugars on the surfaces of erythrocytic membranes, and moving the erythrocytes bonded with the boric acid-magnetic beads under an influence of an electromagnetic force. A device for determining the distribution of glycation of erythrocytic membranes includes a container as a cell for electromagnetic-phoresis, a cathode ray and an anode ray which are connected to a direct current power supply, and a magnetic sheet which is placed outside the bottom of the container. The container has an upper surface containing a cathode hole, an anode hole, a filling hole midway between the cathode hole and the anode hole for a specimen, and an excretory hole for releasing air bubbles. After physiological saline is poured into the container, the cathode ray and the anode ray are respectively inserted into the holes to be soaked in the saline. Subsequently, a specimen of erythrocytes, which are bonded with the boric acid-magnetic beads, is infused into the container through the filling hole.

2 Claims, 8 Drawing Sheets

METHOD AND DEVICE FOR DETERMINING DISTRIBUTION OF GLYCATION OF ERYTHROCYTIC MEMBRANES

BACKGROUND OF THE INVENTION

This invention relates to a method for determining the distribution of glycation of erythrocytic membranes and to a device for use in the method.

The deaths of diabetics are mainly due to angiopathy, so it is important to predict the onset of angiopathy for the successful treatment of diabetes. The conventional daily test for diabetes is conducted in the early morning by mainly measuring fasting blood sugar and glycated hemoglobin A1c (HbA1c). As methods for measuring HbA1c, there are known a colorimetry method (Japanese Patent Application Publication Laid-Open No. 8-122335), a high performance chromatography method (Japanese Patent Application Publication Laid-Open No. 9-178719) and so on.

However, these test results cannot be used to evaluate the degree of cell damage or the angiopathy of diabetics. This is the reason why a new method for diagnosing the degree of cell damage of diabetics having a chronic condition of high blood sugar needed to be developed.

Therefore, the inventors tried to develop a new method for determining the distribution of glycation of erythrocytic membranes which can be used to evaluate the degree of diabetic cell damage and a device for use in such method, and they achieved the present invention.

BRIEF SUMMARY OF THE INVENTION

According to the present invention, a method for determining a distribution of glycation of erythrocytic membranes comprises the steps of providing erythrocytic membranes comprising surfaces containing sugars; providing magnetic beads comprising boric acid groups; bonding the magnetic beads to the sugars on the surfaces of the erythrocytic membranes; and moving the erythrocytes bonded with the magnetic beads under an influence of an electromagnetic force.

A device for determining a distribution of glycation of erythrocytic membranes, wherein the erythrocytes are bonded with boric acid-magnetic beads, is also provided. The device comprises a container to receive a psychological saline solution; a cathode ray and an anode ray, each connected to a direct current power supply; and a magnetic sheet placed outside of a bottom of the container; wherein the container comprises an upper surface having a cathode hole and an anode hole separated by a certain space, a filling hole midway between the cathode hole and the anode hole for a specimen, and an excretory hole for releasing air bubbles; and wherein the cathode ray and the anode ray are inserted into the container through the cathode hole and the anode hole respectively for soaking in the saline solution.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

A method for determining the distribution of glycation of erythrocytic membranes according to the present invention includes the steps of bonding magnetic beads having a boric acid group (hereinafter referred to as boric acid-magnetic beads) with sugars on the surfaces of membranes of erythrocytes, and moving the erythrocytes bonded with the boric acid-magnetic beads under the influence of an electromagnetic force (hereinafter the latter step is referred to as electromagnetic-phoresis).

Figure 1:
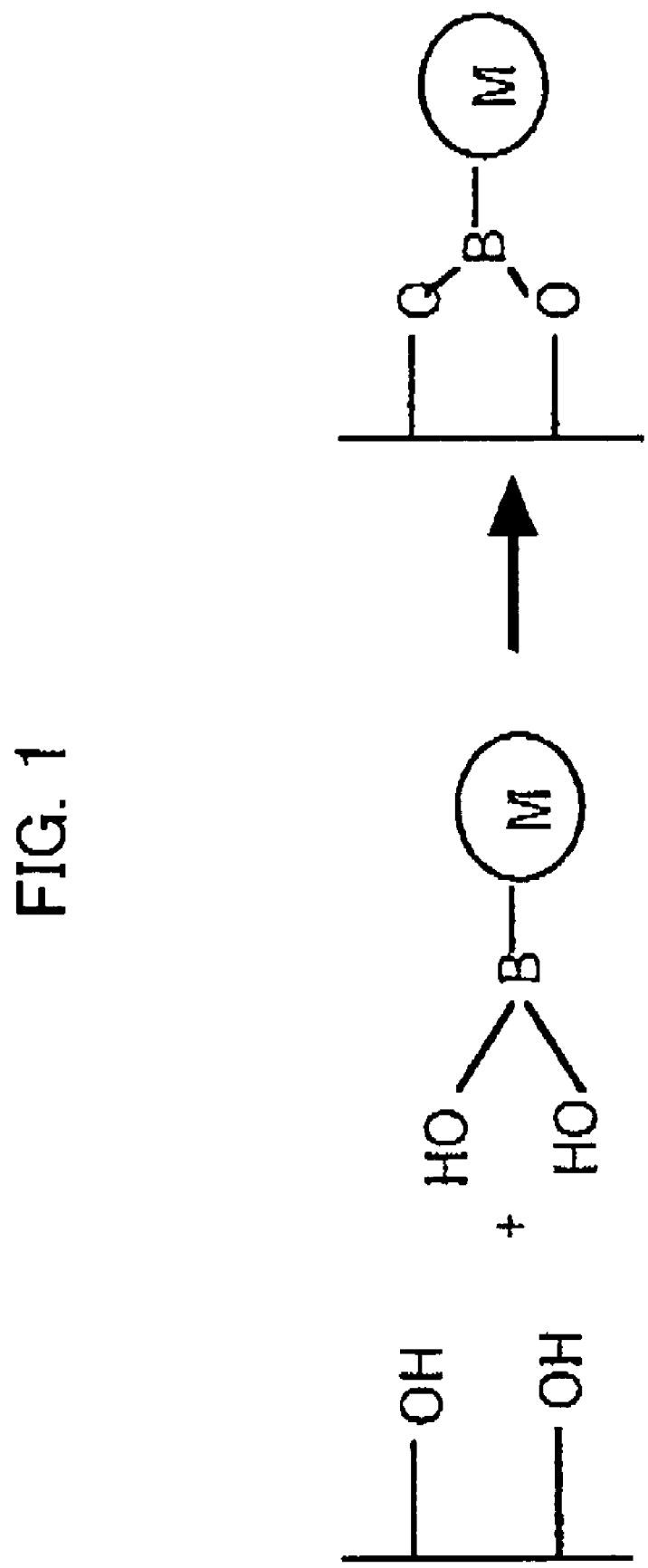
FIG. 1 is a diagrammatic illustration demonstrating how a boric acid-magnetic bead bonds with a sugar according to the present invention.

The principle of the method of the present invention is as follows. The number of diols on the sugar molecules on the surfaces of the erythrocytic membranes is increased as a result of glycation on these surfaces, and the diols are coupled with the boric acid groups of the boric acid-magnetic beads under alkaline conditions. Consequently, the magnetic beads are bonded with the surfaces of the erythrocytic membranes through the boric group, as shown in FIG. 1. The erythrocytes are strongly affected by an external magnetic force to an extent which is proportional to the number of magnetic beads bonded with the membranes of the erythrocytes, such that the electromagnetic-phoresis of the erythrocytes is restricted.

A device for determining the distribution of glycation of erythrocytic membranes according to the present invention includes a container as a cell for electromagnetic-phoresis, a cathode ray and an anode ray which are connected to a direct current power supply, and a magnetic sheet which is placed outside of the bottom of the container. On the upper surface of the container are a cathode hole, an anode hole, a filling hole midway between the cathode hole and the anode hole for a specimen, and an excretory hole for releasing air bubbles. The cathode hole and the anode hole are separated by a certain space, and the excretory hole is provided at an appropriate position on the upper surface of the container. After physiological saline is poured into the container, the cathode ray and the anode ray are inserted into the cathode hole and anode hole, respectively, to be soaked in the saline. Subsequently, a specimen of erythrocytes, which are bonded with the boric acid-magnetic beads, is infused into the container through the filling hole.

Furthermore, the device according to the present invention may have a polytetrafluoroethylene (available as Teflon®, manufactured by E.I. DuPont de Nemours & Co.) sheet to cover the lower inside of the container in order to prevent nonspecific bonding interactions between the erythrocytes and the materials of the container.

Referring to the Figures, the following description will discuss embodiments of the present invention.

As specimens of erythrocytes for the present invention, blood samples collected for an assay of glycated hemoglobin Alc (HbAlc) (the normal range is 4.3-5.8%, determined from a high performance chromatography method) were used.

For use in the present invention, boric acid-magnetic beads were specially synthesized by bonding magnetic beads which have an amino group (1-4 μm i.d., MagnaBind™ Amine Derivatized Beads; made by Pierce Biotechnology, Inc.) with boric acid (made by Wako Pure Chemical Industries, Ltd.) using glutaraldehyde.

The boric acid-magnetic beads were bonded with the erythrocytes as follows. Firstly, the specimen of erythrocytes was added to physiological saline with the decuple volume of the specimen, and centrifuged (3,000 r.p.m., 3 min.). After that, the supernatant liquid was removed to obtain the cleaned erythrocytes. Subsequently, Tricine buffer (pH 9.4) was added to the cleaned erythrocytes, and then the boric acid-magnetic beads were added to them. Finally, the mixed solution was left at room temperature for 2 minutes to react.

Figure 2:
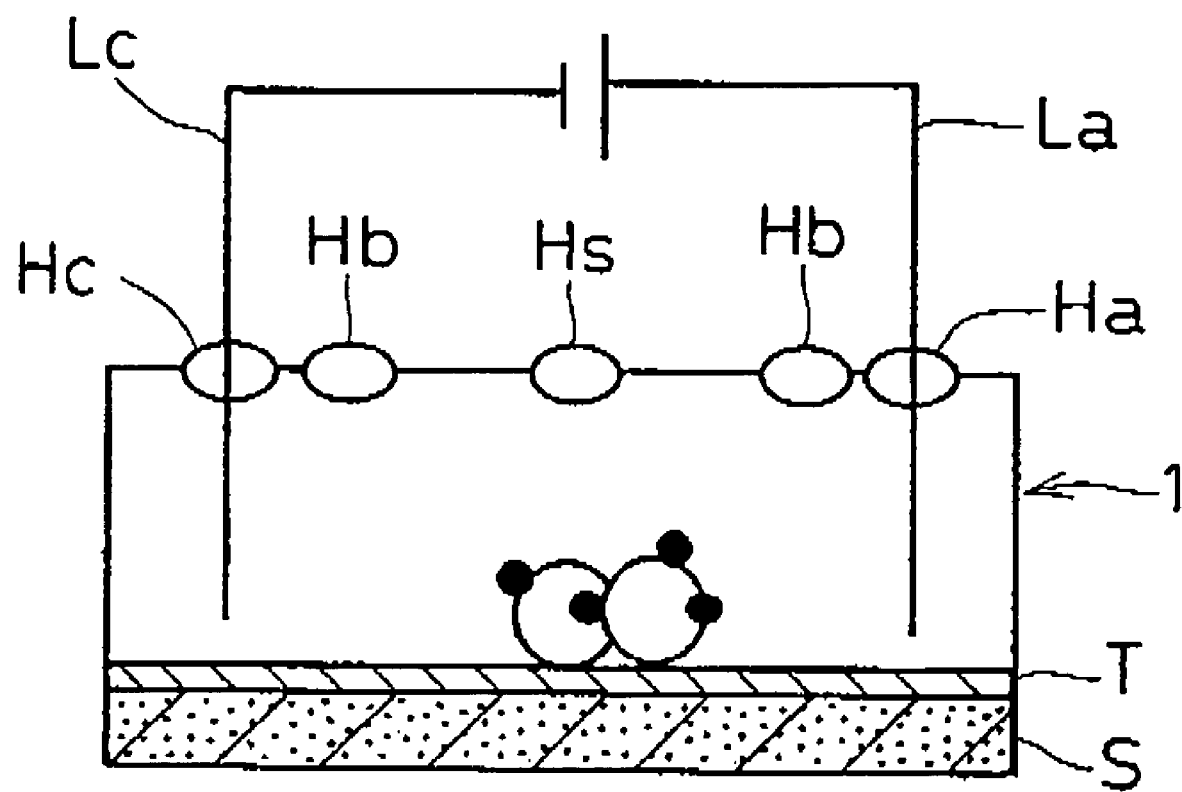
FIG. 2 is a diagrammatic illustration of an electromagnetic-phoresis device according to the present invention.

As shown in FIG. 2, a cell for electromagnetic-phoresis of the present invention was made with a transparent rectangular container 1 (6×60×4 mm, made of polycarbonate). A cathode hole Hc, an anode hole Ha, a filling hole Hs for a specimen, and two excretory holes Hb for releasing air bubbles were provided on the upper surface of the container 1. The diameter of each of the holes was 3 mm. The distances between holes Hc and Hs and holes Hs and Ha were each 26 mm each. The lower inside of the container 1 was covered with a polytetrafluoroethylene (Teflon®, made by DuPont) sheet T in order to prevent nonspecific bonding interactions between the erythrocytes and the materials of the container 1. A cathode ray Lc and an anode ray La (both made of platinum) were connected to a regulated DC power supply (PA250-0.42AL, made by Kenwood Tmi Corporation). The other ends of the cathode ray Lc and the anode ray La were inserted into the above-mentioned cell through the holes Hc and Ha, respectively, to be soaked in the saline, which had been poured into the cell in advance. A magnetic sheet S (ferrite magnet, 300 gauss, 0.8 mm thick, made by MagX Co., Ltd.), which was the same size as the bottom of the cell (6×60 mm), was placed outside the bottom of the cell. A digital camera (Coolpix 995, made by Nikon Corporation) was used for taking a photograph of the electromagnetic-phoresis pattern, and a personal computer (EDi Cube NC610, made by Seiko Epson Corporation) was used for storing a digital image of the photograph.

Immediately after being bonded with the boric acid-magnetic beads, 3 μl of the erythrocytes was infused into the cell for electromagnetic-phoresis through the hole Hs, and a current (4-5 V, 20 mA) was applied to the cell for 7 minutes at room temperature. The physiological saline (pH 7.4) in the cell was used as a solution for the electromagnetic-phoresis.

The electromagnetic pattern of the erythrocytes bonded with the boric acid-magnetic beads was photographed from the upper surface of the cell using a macro-mode of the digital camera. The photographed data were analyzed by a personal computer (PC Station M260RB, made by Sotec Co., Ltd.) with two packages of image analysis software (CS analyzer, made by Atto Corporation, and Photoshop® LE, made by Adobe System Inc.). The electromagnetic-phoresis patterns in color were changed into monochrome by extracting the red brightness in order to make the erythrocytes in the photographs recognizable.

Next, the method of the present invention was carried out using three different external magnetic forces (0, 300, and 850 gauss) to determine the appropriate external magnetic force for restricting the movement of the erythrocytes bonded with the boric acid-magnetic beads.

Figure 3:
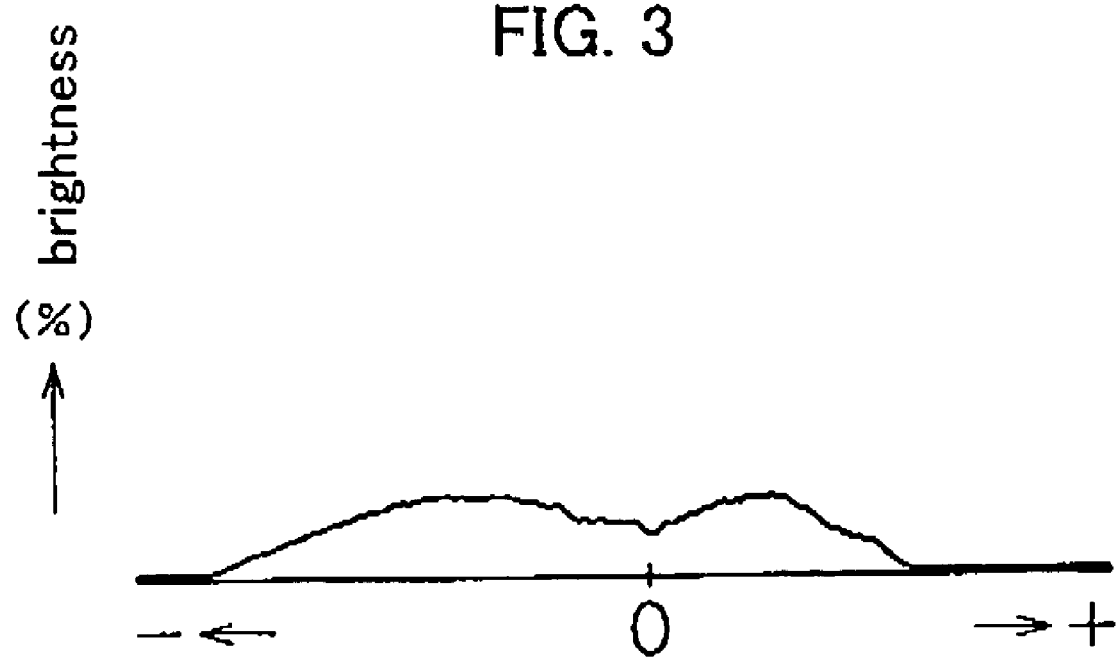
FIGS. 3-5 are electromagnetic-phoresis patterns of erythrocytes bonded with magnetic beads.
Figure 4:
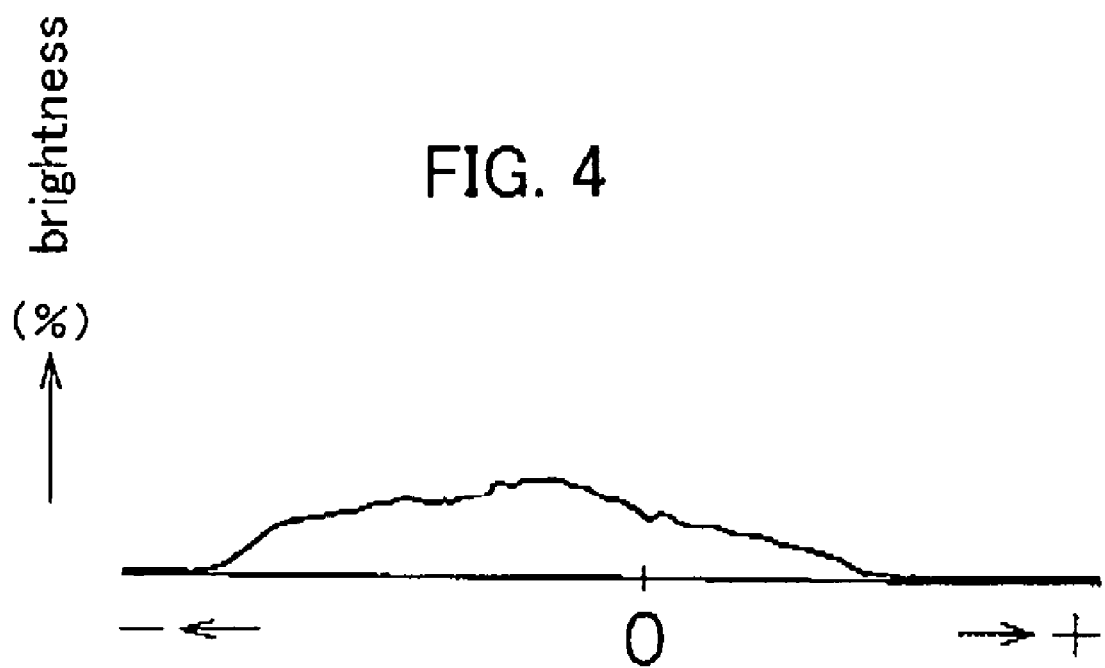
Figure 5:
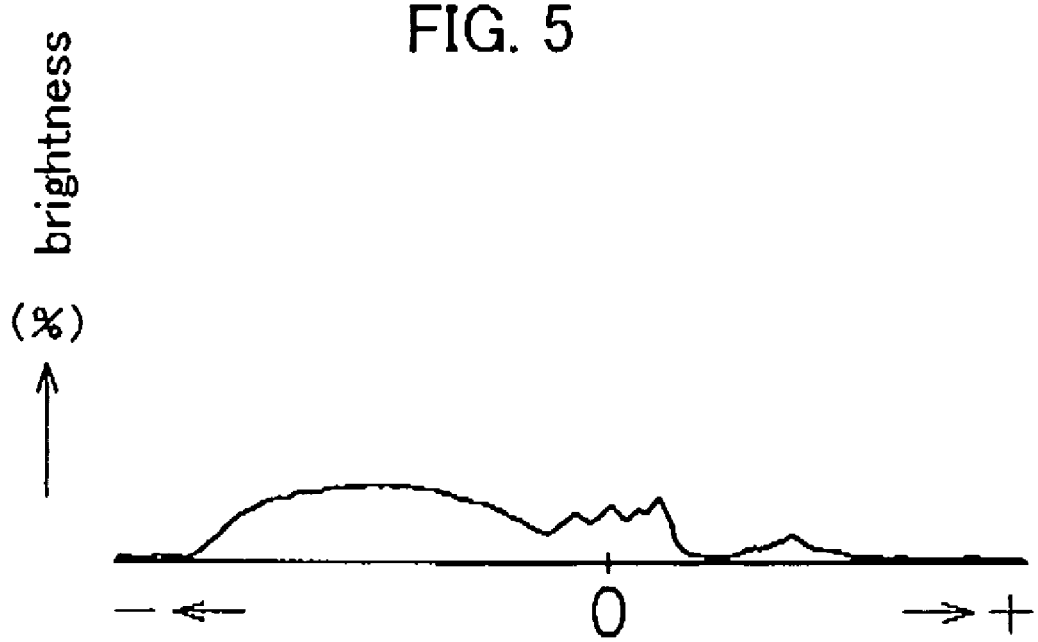

As the 300-gauss magnetic force, the ferrite magnet sheet placed under the cell to cover the outside of the bottom of the cell was used. As the 850-gauss magnetic force, a Magnepiece (diameter 1 cm, M -7, made by Niigata Seiki Co., Ltd.) was used. The center of the Magnepiece was placed exactly at the center point of the hole Hs. In each case, erythrocytes with HbAlc 5.4% were used as a specimen. As a result of the electromagnetic-phoresis under the above described conditions, the electromagnetic-phoresis patterns shown in FIGS. 3-5 were obtained. By analyzing the images of the patterns, it was found that the relative brightness of the erythrocytes remaining at a point of the hole Hs were respectively 7.6% at 0 gauss, 10.1% at 300 gauss, and 11.2% at 850 gauss.

From the above results, it was obvious that the erythrocytes bonded to the boric acid-magnetic beads were strongly drawn toward a place around the hole Hs according to the strength of the external magnetic force. In the present invention, the 300-gauss sheet (the ferrite sheet) was used as the external magnetic force, but it has been proven that a sheet with approximately 300 gauss or more than 300 gauss can also be used.

Furthermore, the patterns of both electrophoresis and electromagnetic-phoresis of the erythrocytes were compared to demonstrate that electromagnetic-phoresis is more appropriate for the present invention. The above-described device was used for electromagnetic-phoresis, and for the electrophoresis, the same device was used without the magnetic sheet placed under the cell.

Figure 6:
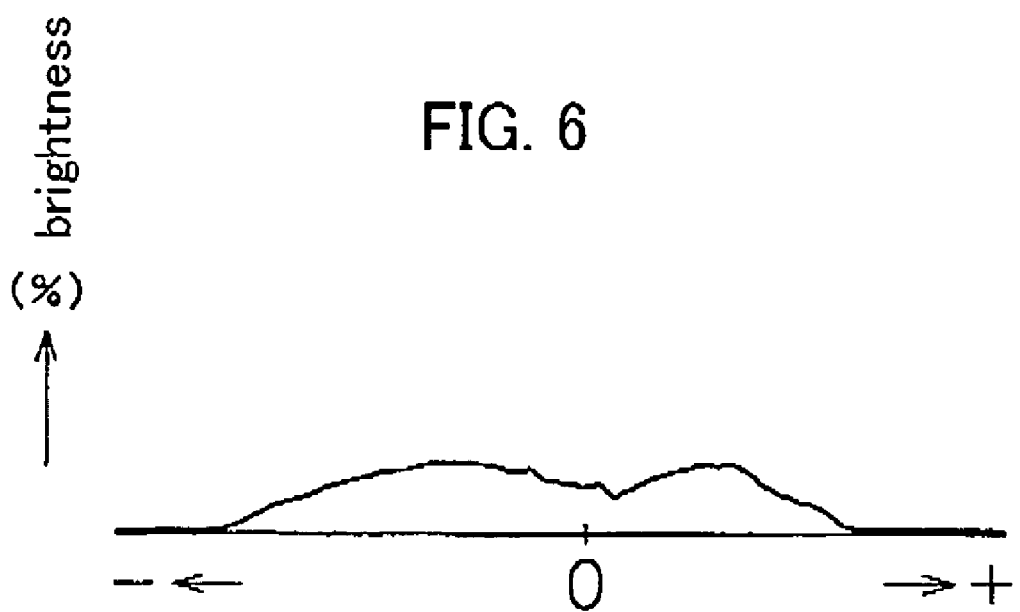
FIGS. 6 and 7 are respectively electrophoresis and electromagnetic-phoresis patterns of erythrocytes having HbA1c of 5.4%.
Figure 7:
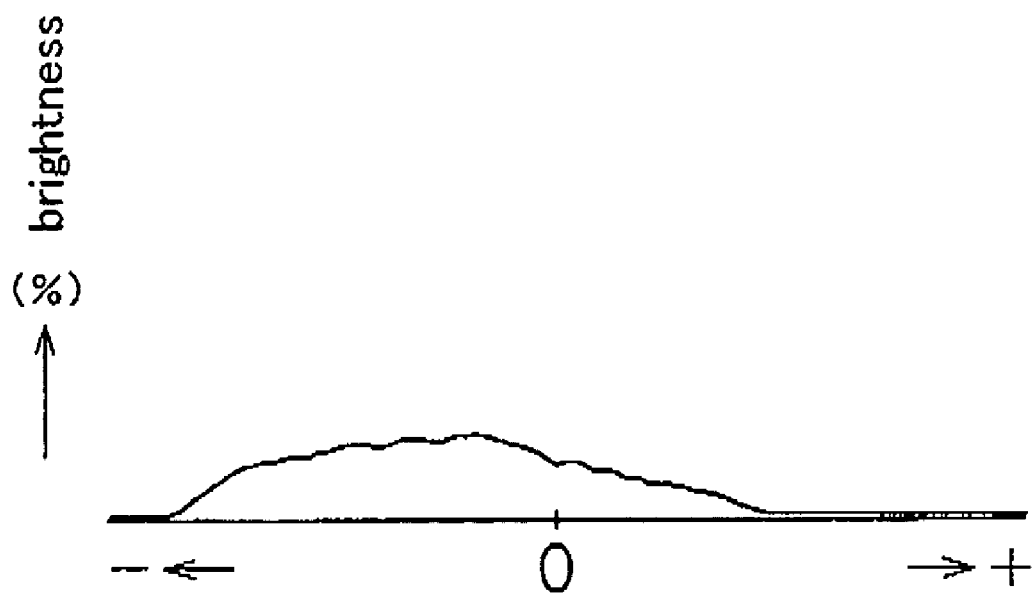

In the case of electrophoresis of erythrocytes with HbAlc of 5.4% (normal blood sugar level), the electrophoresis pattern shown in FIG. 6 was obtained. By analyzing the image of this electrophoresis pattern, it was found that the migration distance to the cathode was −27.8% with a brightness of 58.9%, while the migration distance to the anode was +16.7% with a brightness of 33.6%. Meanwhile, in the case of electromagnetic-phoresis of the same erythrocytes, the electromagnetic-phoresis pattern shown in FIG. 7 was obtained. By analyzing the image of this electromagnetic-phoresis pattern, it was found that the migration distance to the cathode was −26.7% with a brightness of 71.4%, while the migration distance to the anode was +14.4% with a brightness of 18.5%.

Figure 8:
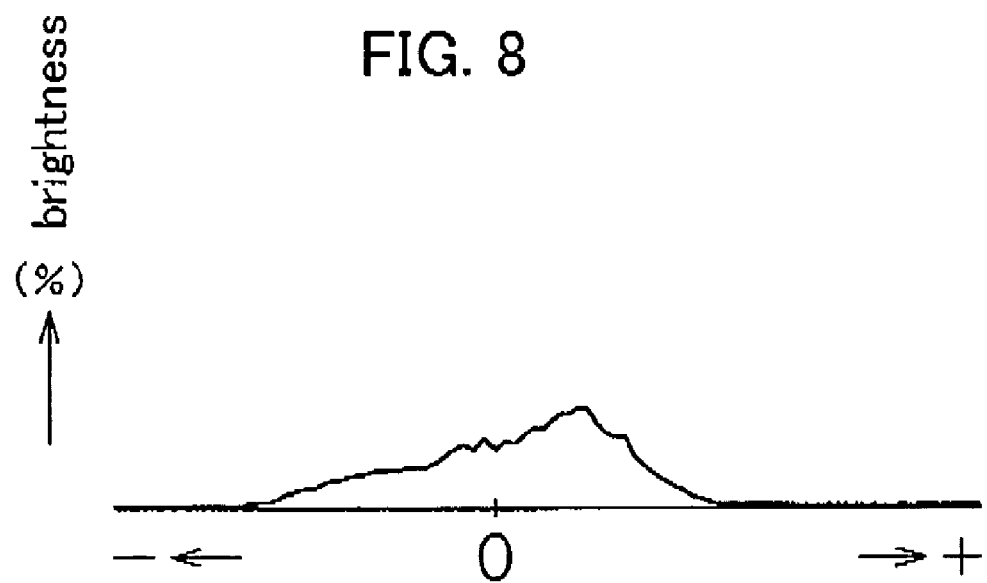
FIGS. 8 and 9 are respectively electrophoresis and electromagnetic-phoresis patterns of erythrocytes having HbA1c of 11.3%.
Figure 9:
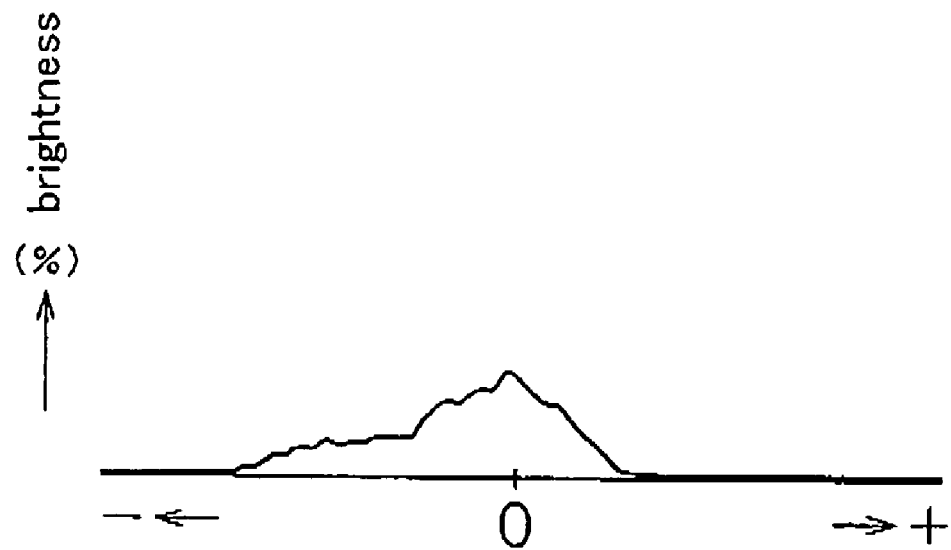
Figure 10:
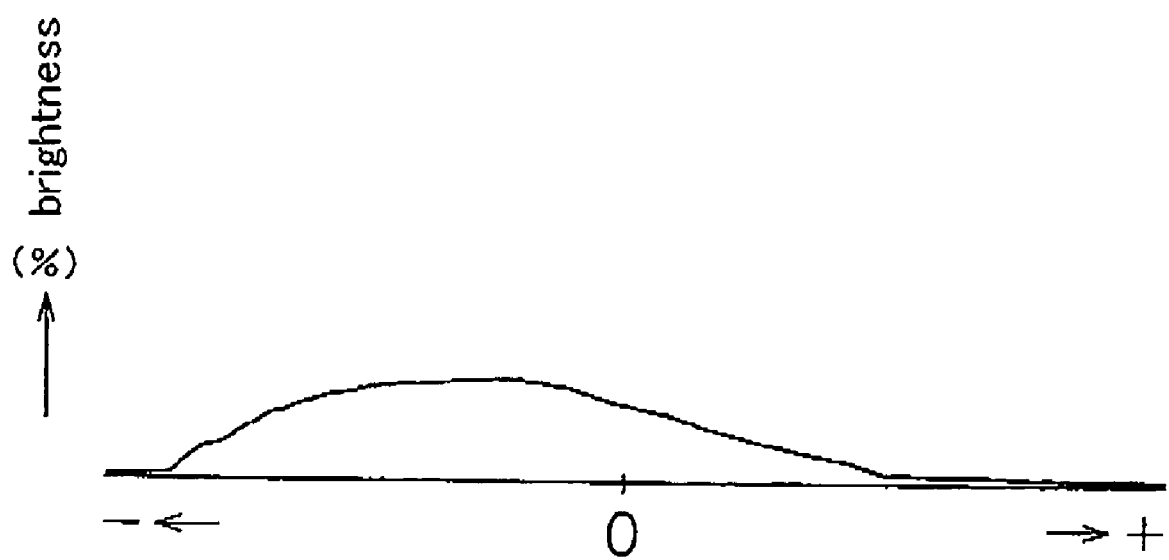
FIGS. 10-14 are electromagnetic-phoresis patterns of erythrocytes with certain degrees of glycation.
Figure 11:
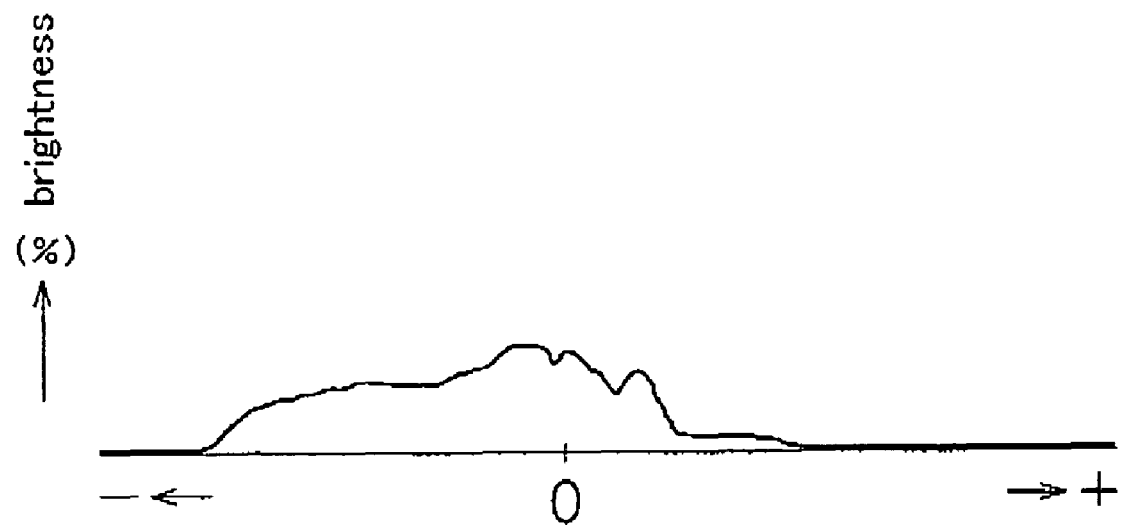
Figure 12:
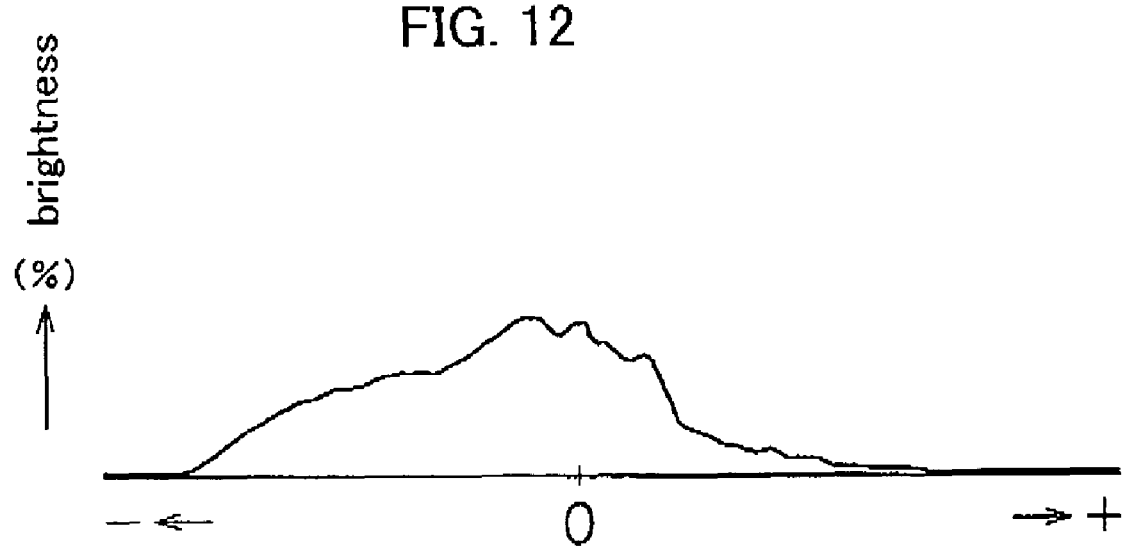
Figure 13:
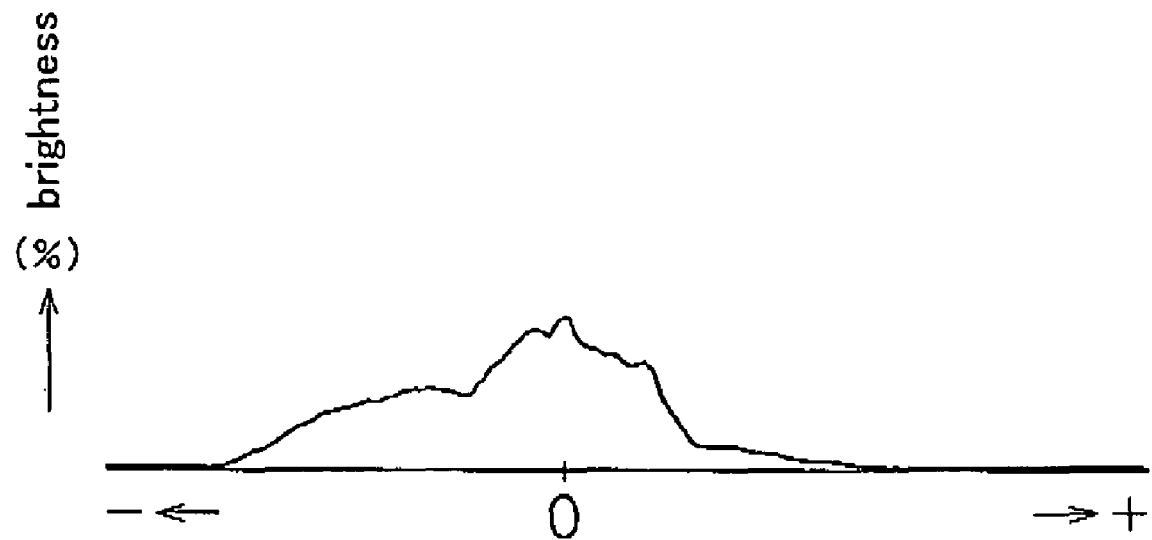
Figure 14:
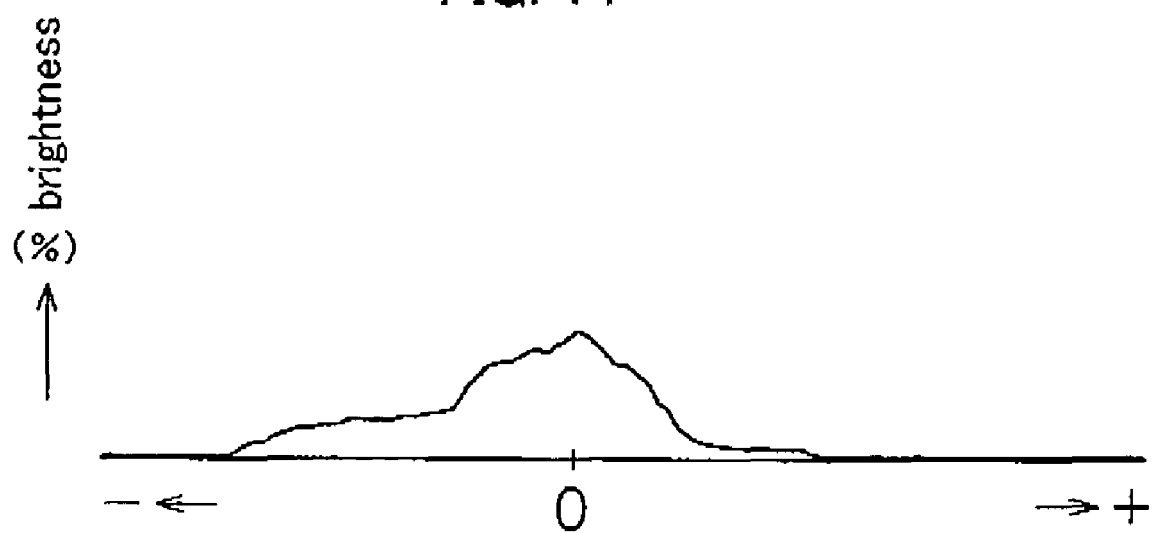

In the case of an electrophoresis of erythrocytes with HbAlc of 11.3% (high blood sugar level), the electrophoresis pattern shown in FIG. 8 was obtained. By analyzing the image of this electrophoresis pattern, it was found that the migration distance to the cathode was −18.3% with a brightness of 32.2%, while the migration distance to the anode was +15.0% with a brightness of 53.9%. Meanwhile, in the case of electromagnetic-phoresis of the same erythrocytes, the electromagnetic-phoresis pattern shown in FIG. 9 was gained. By analyzing the image of this electromagnetic-phoresis pattern, it was found that the migration distance to the cathode was −22.2% with a brightness of 58.9%, while the migration distance to the anode was +16.6% with a brightness of 21.2%.

The above results show that in both cases of the erythrocytes having different blood sugar levels, the migration distances to both the cathode and anode in the electromagnetic-phoresis pattern were shorter than those in the electrophoresis pattern, and this is more clearly seen in the case of erythrocytes with HbA1c of 11.3%. It is considered as the cause of these differences in the migration distance that electrophoresis patterns only show the distribution of electric charge on the surfaces of the erythrocytes, while electromagnetic-phoresis patterns show the distribution of glycation of the erythrocytic membranes.

Next, the present invention was carried out using erythrocytes having different blood sugar levels (HbA1c: 5.4%, 7.7%, 8.6%, 9.3%, and 11.3%), which were bonded with boric acid-magnetic beads, to see the influence of the blood sugar differences upon the electromagnetic-phoresis of the erythrocytes.

As a result, the electromagnetic-phoresis patterns shown in FIGS. 10-14 were obtained by electromagnetic-phoresis. By analyzing the images of these patterns, it was found that the brightness of the erythrocytes at the origin were 10.1% (HbA1c 5.4%), 55.0% (HbA1c 7.7%), 58.8% (HbA1c 8.6%), 59.1% (HbA1c 9.3%) and 69.7% (HbA1c 11.3%), and the migration distances to the cathode were −26.7% (HbA1c 5.4%), −23.9% (HbA1c 7.7%), −25.0% (HbA1c 8.6%), −22.2% (HbA1c 9.3%) and −22.2% (HbA1c 11.3%). The migration distances to the anode were +4.9% (HbA1c 5.4%), +3.0% (HbA1c 7.7%), +2.0% (HbA1c 8.6%), +2.9% (HbA1c 9.3%) and +2.7% (HbA1c 11.3%). As demonstrated by these results, the migration distances to both cathode and anode gradually shortened with the increase of HbA1c.

From these results of electromagnetic-phoresis, it was obvious that the amount of sugar held on the surfaces of the erythrocytic membranes increased as the blood sugar level was increasing.

Therefore, in the method according to the present invention, the change in the amount of glycation of the erythrocytic membranes according to the blood sugar level is used as a new indicator for the control of diabetes, so that it becomes possible to determine the rise in the degree of glycation of the erythrocytic membranes of diabetics having a chronic condition of high blood sugar. Accordingly, this method makes it possible to evaluate the degree of cell damage or the angiopathy of diabetics.

Furthermore, a device for determining the distribution of glycation of erythrocytic membranes according to the present invention realized easy determination of the change in glycation of the erythrocytic membranes according to the blood sugar level.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for determining a distribution of surface glycation of erythrocytic membranes comprising the steps of:
   providing erythrocytes having erythrocytic membranes comprising surfaces containing sugars;
   providing magnetic beads comprising boric acid groups;
   bonding the magnetic beads to the sugars on the surfaces of the erythrocytic membranes;
   moving the erythrocytes bonded with the magnetic beads under an influence of an electromagnetic force;
   collecting an electromagnetic-phoresis pattern; and
   analyzing the pattern to determine the distribution of glycation.

2. The method according to claim 1, wherein the electromagnetic force has a strength of 300 or 850 gauss.

* * * * *